United States Patent [19]

Gehret et al.

[11] Patent Number: 4,560,770
[45] Date of Patent: Dec. 24, 1985

[54] PESTICIDAL COMPOSITIONS BASED ON N-PYRROLYLPHENYL-N'-BENZOYLUREA COMPOUNDS

[75] Inventors: Jean-Claude Gehret, Aesch; Kurt Gubler, Riehen, both of Switzerland

[73] Assignee: Ciba-Geigy Corporation, Ardsley, N.Y.

[21] Appl. No.: 574,798

[22] Filed: Jan. 30, 1984

[30] Foreign Application Priority Data

Feb. 9, 1983 [CH] Switzerland .............................. 726/83

[51] Int. Cl.$^4$ ...................... C07D 207/04; C08K 5/21
[52] U.S. Cl. ....................................... 548/561; 524/147
[58] Field of Search .......................... 548/561; 524/147

[56] References Cited

U.S. PATENT DOCUMENTS

| | | | |
|---|---|---|---|
| 2,770,628 | 11/1956 | Bortnick et al. | 548/561 |
| 3,558,652 | 1/1971 | Teotino et al. | 548/561 |
| 3,631,037 | 12/1971 | Duncan et al. | 548/561 |
| 4,369,276 | 1/1983 | Wirth et al. | 524/147 |
| 4,369,277 | 1/1983 | Wirth et al. | 524/147 |

FOREIGN PATENT DOCUMENTS

| | | |
|---|---|---|
| 832304 | 2/1976 | Belgium . |
| 843906 | 1/1977 | Belgium . |
| 844066 | 1/1977 | Belgium . |
| 2123236 | 12/1971 | Fed. Rep. of Germany . |
| 2504982 | 8/1976 | Fed. Rep. of Germany . |
| 2537413 | 3/1977 | Fed. Rep. of Germany . |
| 2601780 | 7/1977 | Fed. Rep. of Germany . |
| 2726684 | 1/1979 | Fed. Rep. of Germany . |
| 2134518 | 8/1984 | United Kingdom . |

OTHER PUBLICATIONS

Wellinga et al., "Synthesis and Laboratory Evaluation of 1-(2,6-Disubstituted Benzoyl)-3 . . . ", J. Agr. Food Chem., 21:348, (1973).

*Primary Examiner*—Herbert S. Cockeram
*Attorney, Agent, or Firm*—Edward McC. Roberts; Irving M. Fishman

[57] ABSTRACT

Novel substituted N-pyrrolylphenyl-N'-benzoylurea compounds of the formula

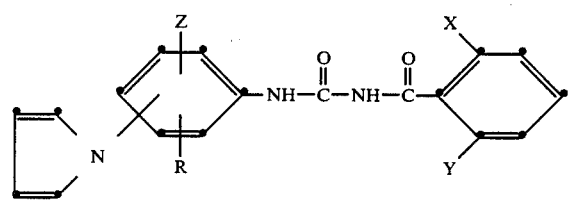

in which
X and Y independently of one another are each hydrogen or halogen,
R is hydrogen or halogen, and
Z is hydrogen, halogen or methyl.

The compounds have valuable properties for controlling pests, such as phytoparasitic and zooparasitic insects and members of the order Acarina, including in particular ectoparasites.

8 Claims, No Drawings

PESTICIDAL COMPOSITIONS BASED ON N-PYRROLYLPHENYL-N'-BENZOYLUREA COMPOUNDS

The present invention relates to substituted N-pyrrolylphenyl-N'-benzoylureas, to processes for producing them, to pesticidal compositions which contain these compounds as active ingredients, and to the use thereof for controlling harmful insects, and members of the order Acarina.

The N-pyrrolylphenyl-N'-benzoylureas according to the invention have the formula I

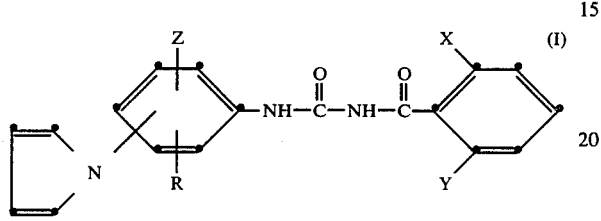

in which
X and Y independently of one another are each hydrogen or halogen,
R is hydrogen or halogen, and
Z is hydrogen, halogen or methyl.

Preferred as active ingredients of pesticidal compositions are those compounds of the formula I in which X and Y independently of one another are each hydrogen, fluorine or chlorine, R is hydrogen or chlorine, and Z is hydrogen, chlorine or methyl.

Having particularly good properties for the control of pests are furthermore the compounds of the following restricted formula Ia

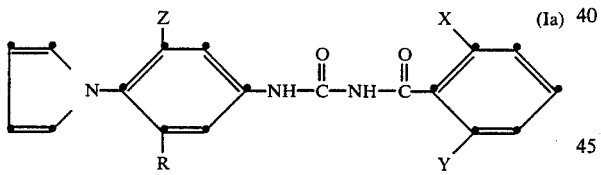

in which X is fluorine or chlorine, Y is hydrogen or fluorine, and R and Z are chlorine.

Further preferred active ingredients by virtue of their excellent action against pests are the following individual compounds embraced by the formula I:
$N^1$-[3,5-dichloro-4-pyrrolo(1)]-phenyl-$N^2$-2,6-difluorobenzoylurea,
$N^1$-[3,5-dichloro-4-pyrrolo(1)]-phenyl-$N^2$-2-fluoro-6-chlorobenzoylurea,
$N^1$-[3,5-dichloro-4-pyrrolo(1)]-phenyl-$N^2$-2-chlorobenzoylurea, and
$N^1$-[3,5-dichloro-4-pyrrolo(1)]-phenyl-$N^2$-2-fluorobenzoylurea.

The compounds of the formula I are novel, but are obtainable by processes known per se (cp., inter alia, the German Offenlegungsschriften Nos. 2,123,236 and 2,601,780).

A compound of the formula I can thus be obtained for example
(a) by reaction of a compound of the formula II

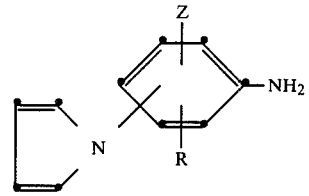

with a compound of the formula III

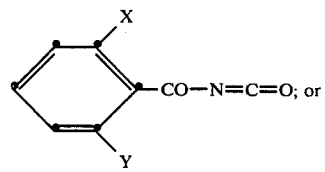

(b) by reaction of a compound of the formula IV

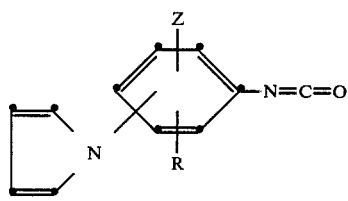

with a compound of the formula V

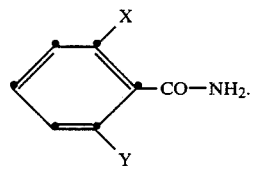

In the formulae II, III, IV and V given above, the symbols R, Z, X and Y have the meanings defined under the formula I.

The mentioned processes (a) and (b) are preferably performed under normal pressure and in the presence of an organic solvent or diluent. Suitable solvents or diluents are for example: ethers and ethereal compounds, such as diethyl ether, dipropyl ether, dibutyl ether, dioxane, dimethoxyethane and tetrahydrofuran; N,N-dialkylated carboxylic acid amides; aliphatic, aromatic as well as halogenated hydrocarbons, especially benzene, toluene, xylene, chloroform, methylene chloride, carbon tetrachloride and chlorobenzene; nitriles, such as acetonitrile or propionitrile; dimethyl sulfoxide; and also ketones, for example acetone, methyl ethyl ketone, methylisopropyl ketone and methylisobutyl ketone. Process (a) is performed in general at a temperature of between −10° and 100° C., preferably between 15° and 25° C., optionally in the presence of an organic base, for example triethylamine. Process (b) is carried out at a temperature of between 0° and 120° C., preferably at the boiling point of the employed solvent, and optionally in the presence of an organic base, such as pyridine, and/or with the addition of an alkali metal or alkaline-earth metal, preferably sodium.

The starting materials of the formulae II, III, IV and V given in the foregoing are known or, in cases where they are novel, can be produced by methods analogous to known methods. The aniline derivatives of the formula II can thus be produced by reduction or catalytic hydrogenation of the corresponding nitro compounds [cp., for example, Rec. 21, 271 (1902); J. Am. Soc. 68, 1604 (1946); J. Org. Chem. 11, 378 (1946); and Rec. 79, 995 (1970)]. The isocyanates of the formula IV are obtainable by reaction of the substituted aniline derivatives of the formula II with phosgene by use of customary procedures. The compounds of the formula III can be obtained as follows (cp. J. Agr. Food Chem. 21(3). 348–993; 1973):

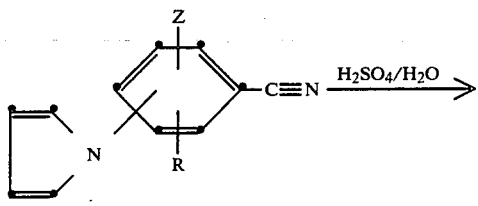

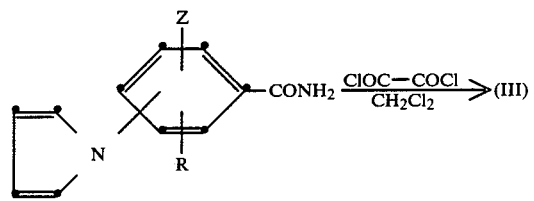

The symbols R and Z in the above formulae have the meanings defined under the formula I.

The introduction of the pyrrole ring can be performed, starting with correspondingly substituted nitraniline derivatives, by the following known process (cp. Org. Synthes. 47, 81–82):

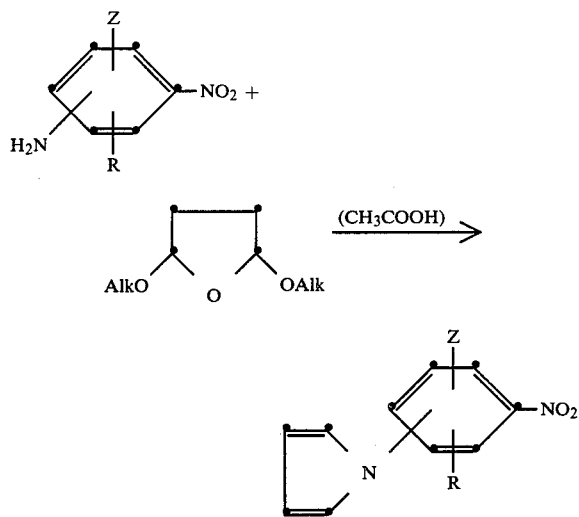

In the above formulae, R and Z have the meanings given under the formula I, and Alk denotes lower alkyl.

The nitro compounds thus obtained can then be converted, as mentioned above, into the corresponding aniline derivatives.

The novel starting compounds, from which are obtained the valuable active substances of the formula I, likewise form subject matter of the present invention.

It is already known that specific N-phenyl-N'-benzoyl-ureas have insecticidal properties (cp. German Offenlegungsschriften Nos. 2,123,236, 2,504,982, 2,537,413, 2,601,780 and 2,726,684; the Belgian Patent Specifications Nos. 832,304, 843,906, 844,066 and 867,046; and also the U.S. Pat. No. 4,089,975). Furthermore, from J. Agr. Food Chem. 21, No. 3, 348ff. (1973) are known substituted N-phenyl-N'-2,6-dichlorobenzoylureas, to which are ascribed insecticidal properties. It has however been shown that the benzoylureas described in the aforementioned publications do not meet to the desired extent the requirements in practice with regard to the control of pests.

It has now been found that, compared with the compounds cited above, the compounds of the formula I according to the present invention surprisingly exhibit an excellent degree of activity as pesticidal active substances whilst having high tolerance to plants and negligible toxicity to warm-blooded animals. The novel compounds are suitable in particular for the control of pests which infest plants and animals.

The compounds of the formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera.

Besides having a very favourable action in the case of their preferred application for the control of flies, for example *Musca domestica*, and blowflies (such as *Lucilia sericata* and *Lucilia cuprina*) and also mosquitoes, the compounds of the formula I have an excellent action also against insects that damage productive and ornamental plants by eating. Particularly readily controllable by the novel compounds are insect pests in cotton crops, (for example *Spodoptera littoralis* and *Heliothis virescens*) and those in vegetable crops (for example *Leptinotarsa* and *Pieris brassicae*). Of the spectrum of activity of the compounds of the formula I, a feature to be particularly emphasised is their larvicidal effectiveness. When for example compounds of the formula I are taken up with the feed by adult insect pests, there is observed a great reduction in the rate of hatching of the larvae and a suppression of the development of the larval stages, factors which lead to an extensive decimation of the populations of the treated insect pests.

The compounds of the formula I are suitable also for controlling ectoparasites on both domestic and productive animals, among which insects are meant, in addition to the ones mentioned above, also those of the order Acarina. The control of pests can be carried out by the treatment of animals, livestock housing and pasture land.

As active ingredients of compositions, the compounds of the formula I according to the invention are suitable, by virtue of the different forms in which the compositions are made up, for controlling in a variety of ways parasites on animals or in the vicinity of animals, for example in livestock housing. The compounds can thus be applied for example in cattle dips, spray races, pour-on solutions or manual sprayers. They can also be used with great success for the treatment of animal faeces by means of the feed-through method, and for the hygienic treatment of manure in livestock housing.

The action of the compounds according to the present invention or of the compositions containing them can be considerably broadened and adapted to suit prevailing conditions by the addition of other insecticides and/or acaricides. Suitable additives are for example the following active substances: organic phosphorus compounds, formamidines, ureas, carbamates, chlorinated hydrocarbons and triazine derivatives.

The compounds of the formula I can advantageously be combined with substances having a biocidally intensifying effect. Examples of such compounds are, inter alia: piperonyl butoxide, propynyl ethers, propynyl oximes, propynyl carbamates and propynyl phosphonates or 2-(3,4-methylenedioxyphenoxy)-3,6,9-trioxaundecane.

The compounds of the formula I can be used either on their own or together with suitable carriers and/or additives. Suitable carriers and additives can be solid or liquid and they correspond to the substances customarily employed in formulation practice, for example: natural or regenerated substances, solvents, dispersing agents, wetting agents, adhesives, thickeners, binders and/or fertilisers. For application, the compounds of the formula I can be processed, by the usual formulation procedures which are a part of common knowledge in the field of application techniques, into the form of dusts, emulsion concentrates, granulates, dispersions, sprays or solutions. Also to be mentioned are cattle dips, spray races and pour-on solution, in which aqueous preparations are used. These forms of application are particularly suitable for controlling zooparasitic pests.

The compositions according to the invention are produced, in a manner known per se, by the intimate mixing and/or grinding of active ingredients of the formula I with the appropriate carriers, optionally with the addition of dispersing agents and solvents inert to the active ingredients. The active ingredients can be made up and used in the following forms:

solid preparations: dusts, scattering agents and granulates (coated granulates, impregnated granulates and homogeneous granulates);

liquid preparations:
  (a) water-dispersible concentrates of active ingredient: wettable powders, pastes and emulsions;
  (b) solutions.

The content of active ingredient in the compositions described above is between 0.1 and 95% by weight.

The active ingredients of the formula I can be formulated for example as follows:

Dusts

The following substances are used to produce (a) a 5% dust and (b) a 2% dust:

(a)

5 parts of active ingredient, and
95 parts of talcum;

(b)

2 parts of active ingredient,
1 part of highly dispersed silicic acid, and
97 parts of talcum.

The active ingredients are mixed and ground with the carriers.

Granulate

The following substances are used to produce a 5% granulate:
5 parts of active ingredient,
0.25 parts of epoxidised vegetable oil,
0.25 part of cetyl polyglycol ether,
3.50 parts of polyethylene glycol, and
91 parts of kaolin (particle size 0.3–0.8 mm).

The active ingredient is mixed with the epoxidised vegetable oil, the mixture is dissolved in 6 parts of acetone, and the polyethylene glycol and cetyl polyglycol ether are then added. The solution thus obtained is sprayed onto kaolin, and the acetone is subsequently evaporated off in vacuo.

Wettable powders

The following constituents are used to produce (a) a 40% wettable powder, (b) and (c) a 25% wettable powder and (d) a 10% wettable powder:

(a)

40 parts of active ingredient,
5 parts of sodium lignin sulfonate,
1 part of sodium dibutyl-naphthalene sulfonate,
54 parts of silicic acid;

(b)

25 parts of active ingredient,
4.5 parts of calcium lignin sulfonate,
1.9 parts of Champagne chalk/hydroxyethyl cellulose mixture (1:1),
1.5 parts of sodium dibutyl-naphthalene sulfonate,
19.5 parts of silicic acid,
19.5 parts of Champagne chalk, and
28.1 parts of kaolin;

(c)

25 parts of active ingredient,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselguhr, and
46 parts of kaolin; and (d)

10 parts of active ingredient,
3 parts of a mixture of the sodium salts of saturated fatty alcohol sulfates,
5 parts of naphthalenesulfonic acid/formaldehyde condensate, and
85 parts of kaolin.

The active ingredients are intimately mixed in suitable mixers with the additives, and the mixture is ground in appropriate mills and rollers. There are obtained wettable powders which can be diluted with water to obtain suspensions of the concentration required.

Emulsifiable concentrates

The following substances are used to produce (a) a 10%, (b) a 25% and (c) a 50% emulsifiable concentrate:

(a)

10 parts of active ingredient,
3.4 parts of epoxidised vegetable oil,
3.4 parts of a combination emulsifier consisting of fatty alcohol polyglycol ether and alkylaralkylsulfonate/calcium salts,
40 parts of dimethylformamide, and
43.2 parts of xylene;

(b)

25 parts of active ingredient,
2.5 parts of epoxidised vegetable oil,
10 parts of an alkylarylsulfonate/fatty alcohol/polyglycol ether mixture,
5 parts of dimethylformamide, and
57.5 parts of xylene; and (c)

50 parts of active ingredient,
4.2 parts of tributylphenol-polyglycol ether,
5.8 parts of calcium dodecylbenzenesulfonate,
20 parts of cyclohexanone, and
20 parts of xylene.

Emulsions of any desired concentration can be produced from such concentrates by dilution with water.

Sprays

The following constituents are used to produce (a) a 5% spray and (b) a 95% spray:

(a)

5 parts of active ingredient,
1 part of epoxidised vegetable oil,
94 parts of ligroin (boiling limits 160°–190° C.);

(b)

95 parts of active ingredient,
5 parts of epoxidised vegetable oil.

EXAMPLE 1

Production of
$N^1$-[3,5-dichloro-4-pyrrolo(1)]-phenyl-$N^2$-2,6-difluorobenzoylurea (1a) 3,5-Dichloro-4-pyrrolonitrobenzene To 62.1 g (0.3 mol) of 2,6-dichloro-4-nitroaniline in 500 ml of glacial acetic acid are added, at room temperature, 43.6 g (0.33 mol) of 3,5-dimethoxytetrahydrofuran. The mixture is slowly heated to 105° C.; it is stirred for 1½ hours at this temperature, and subsequently further stirred overnight at room temperature. The dark solution is filtered through Hyflo and then concentrated in a rotary evaporator. The crude crystals obtained are well stirred up in ice-water, filtered off and washed with water. After treatment with active charcoal, the substance obtained from ethanol is recrystallised; yield: 47.7 g (61.8%) of light-coloured crystals having a melting point of 91°–93° C.

(1b) 3,5-Dichloro-4-pyrroloaniline 47.7 g (0.18 mol) of 3,5-dichloro-4-pyrrolonitrobenzene are hydrogenated with 10 g of Raney nickel at room temperature in tetrahydrofuran. After filtration, the brownish solution is concentrated in a rotary evaporator. The beige crystals obtained are suspended in ice-water, filtered off, washed with hexane and dried in vacuo at 40° C.; yield: 39.9 g (94.8%) of light-coloured crystals having a melting point of 169°–171° C.

(1c) 2,6-Difluorobenzamide

To 240 g of concentrated sulfuric acid and 24 ml of water are added dropwise, at room temperature, 100 g (0.72 mol) of 2,6-difluorobenzonitrile. The reaction mixture is stirred at 80°–85° C. for 12 hours, and then poured into 1.2 kg of ice-water; the mixture is stirred for 30 minutes and subsequently filtered. The crystals are washed neutral with water, and are afterwards dried at 85° C. in vacuo; yield: 91.0 g (80.6%), melting point: 140°–141.5° C.

(1d) 2,6-Difluorobenzoylisocyanate 36.1 g (0.23 mol) of 2,6-difluorobenzamide are suspended in 360 ml of methylene chloride, and 53.7 g (0.42 mol) of oxalyl chloride are then added dropwise in the course of 20 minutes. After the release of hydrochloric acid has finished, the mixture is well stirred overnight under reflux. The solvent is subsequently distilled off, and the residue is distilled through a 10 cm Vigreux column at about 80° C./0.3 mm; yield 37.4 g (89%) of a slightly yellow liquid.

(1e)
$N^1$-[3,5-Dichloro-4-pyrrolo(1)]-phenyl-$N^2$-2,6-difluorobenzoylurea 10.8 g (0.048 mol) of 3,5-dichloro-4-pyrroloaniline in 600 ml of diethyl ether are added dropwise at room temperature, within one hour, to 10.45 g (0.057 mol) of 2,6-difluorobenzoyl-isocyanate in 200 ml of diethyl ether. The temperature is held at 22°–24° C. and, after a short time, a fine precipitate forms. The reaction mixture is further stirred overnight, and subsequently filtered. The beige precipitate is washed with hexane, and dried at 40° C. in vacuo; yield 15.1 g (77.4%); melting point: 235°–237° C.

The following compounds are produced by procedures analogous to those described in the foregoing:

TABLE 1

| No. | (pyrrole position) | R | Z | X | Y | Melting point [°C.] |
|---|---|---|---|---|---|---|
| 1 | 4- | H | H | F | F | 240–242 |
| 2 | 4- | 3-Cl | 5-Cl | F | F | 235–237 |
| 3 | 4- | H | 5-CH$_3$ | F | F | 204–206 |
| 4 | 4- | 3-Cl | 5-Cl | H | Cl | 203–204,5 |
| 5 | 4- | 3-Cl | 5-Cl | H | F | 232–233 |
| 6 | 4- | 3-Cl | 5-Cl | Cl | Cl | 235–237 |
| 7 | 4- | 3-Cl | 5-Cl | F | Cl | 232–234 |
| 8 | 2- | H | H | F | F | 179–181 |
| 9 | 3- | H | 4-CH$_3$ | F | Cl | 198–200 |
| 10 | 2- | H | H | Cl | Cl | 191–193 |
| 11 | 2- | H | 5-Cl | F | F | 212–214 |

EXAMPLE 2

Action against *Lucilia Sericata* (blowfly)

1 ml of an aqueous suspension or solution of the active ingredient, with a content of active ingredient of 1000 ppm, is mixed with a special larval culture medium at 50° C. in such a manner that, in a dilution series, homogeneous mixtures of 250, 100, 50 and 10 ppm of active ingredient are obtained. Specimens each having about 30 freshly emerged larvae (stage I) are then brought into contact with the prepared larval culture medium. The mortality rate is assessed after 4 days.

Compounds according to Example 1 and Table 1 exhibit in this test a good action. The compounds Nos. 2, 4, 5, 6 and 7 result in a 100% mortality rate at a concentration of active ingredient of 10 ppm, whilst the remaining compounds are fully effective at 250 ppm.

EXAMPLE 3

Action against *Lucilia cuprina* (blowfly)

1 ml of an aqueous suspension or solution of the active ingredient, with a content of active ingredient of 1000 ppm, is mixed with a special larval culture medium at 50° C. in such a manner that, in a dilution series, homogeneous mixtures containing 250, 100, 50 and 10 ppm of active ingredient are obtained. Specimens each having about 30 freshly emerged larvae (stage I) are then brought into contact with the prepared larval culture medium, and after 4 days an assessment of the resulting mortality rate is made.

Compounds according to Example 1 and Table 1 exhibit in this test a good action. The compounds Nos. 2, 4, 5, 6 and 7 effect a 100% mortality rate at a concentration of active ingredient of 10 ppm, whilst the remaining compounds are fully effective at 250 ppm.

EXAMPLE 4

Action against *Musca domestica*

50 g of freshly prepared CSMA nutrient medium for maggots are weighed off into each of a series of beakers. A specific amount of a 1% (by weight) acetonic solution of the respective active ingredient is transferred by pipette to the nutrient medium in each beaker. After a thorough mixing of the nutrient medium, the acetone is allowed to evaporate off for at least 20 hours. There are then deposited per active ingredient and concentration in each case 25 one-day-old Musca domestica maggots into each beaker containing the treated nutrient medium. After completion of pupation, the formed pupae are separated from the nutrient medium by flushing with water, and placed into vessels closed with perforated lids. The pupae flushed out per batch are counted (toxic effect of the active ingredient on the development of the maggots), and after 10 days the number of flies which have emerged from the pupae is determined.

Compounds according to Example 1 and Table 1 effected a 100% mortality rate.

EXAMPLE 5

Action against *Aëdes aegypti*

Sufficient of a 0.1% acetonic solution of the respective active ingredient is transferred by pipette to the surface of 150 ml of water in a container to obtain concentrations in each case of 10, 5 and 1 ppm. After the acetone has been evaporated off, 30-40 three-day-old Aëdes larvae are placed into the container, and the mortality rate is ascertained after 1, 2 and 5 days.

Compounds according to Example 1 and Table 1 result in this test in a mortality rate of 100% at all three concentrations.

EXAMPLE 6

Action on *Spodoptera littoralis* and *Heliothis virescens* (larvae and eggs)

Three cotton plants about 15-20 cm in height and grown in pots are treated with a sprayable liquid preparation of the respective active ingredient to be tested. After the drying of the applied coating, the potted plants are placed into a tin container of about 20 liters capacity, which is covered with a glass plate. The humidity inside the covered container is controlled in a manner ensuring that no condensation water is formed, and direct light falling onto the plants is avoided. The three plants are then infested in all as follows:

(a) 50 larvae of *Spodoptera littoralis* and *Heliothis virescens*, respectively, of the first larval stage;
(b) 20 larvae of *Spodoptera littoralis* and *Heliothis virescens*, respectively, of the third larval stage, and
(c) two coatings of eggs of *Spodoptera littoralis* and *Heliothis virescens*, respectively, 2 leaves of a plant being in each case enclosed in a plexiglass cylinder sealed at each end with gauze, and two coatings of eggs of Spodoptera, or a portion of a cotton-plant leaf on which are deposited eggs of Heliothis, are added to the enclosed leaves.

An evaluation, using untreated control plants as a comparison, is made after 4 and 5 days on the basis of the following criteria:

(a) number of living larvae,
(b) inhibition of larval development and shedding,
(c) damage caused by eating (scraping and hole damage),
(d) hatching rate (number of larvae which have emerged from the eggs).

The compounds according to Example 1 and Table 1 exhibit a good overall effectiveness in this test. The hatching rate is less than 5%, and no adult organisms develop from the living larvae remaining.

EXAMPLE 7

Ovicidal action on *Epilachna varivestis* (Mexican bean beetle)

20% by weight of active ingredient, 70% by weight of xylene and 10% by weight of a mixture of a reaction product of an alkylphenol with ethylene oxide and calcium dodecylbenzenesulfonate are mixed together, and from this concentrate are produced, in a dilution series, aqueous emulsions containing 800, 400 and 200 ppm, respectively, of active ingredient.

In each case about 100 eggs of *Epilachna varivestis*, freshly deposited on Phaseolus vulgaris leaves, are moistened with the aqueous emulsions described above (concentrations of 800, 400 and 200 ppm, respectively, of active ingredient), and slightly dried. The treated clusters of eggs are kept in a ventilated vessel until the simultaneously deposited but untreated control eggs have hatched, An evaluation is made under a binocular microscope with regard to the percentage mortality rate achieved.

Compounds according to Example 1 and Table 1 exhibit a good action in this test. The compounds Nos. 2, 4, 5, 6 and 7 effect a 100% mortality rate at a concentration of active ingredient of 200 ppm, whilst the remaining compounds are fully effective at 800 ppm.

EXAMPLE 8

Ovicidal action on *Heliothis virescens* and *Leptinotarsa decemlineata*

Corresponding proportions of a wettable pulverulent formulation containing 25% by weight of the active ingredient to be tested are mixed with specific amounts of water to give aqueous emulsions of increasing active-ingredient concentrations of 200, 400 and 800 ppm. One-day-old clusters of eggs of Heliothis deposited on cellophane and of Leptinotarsa deposited on potato leaves are immersed for three minutes in these emulsions containing the active ingredient to be tested, and are then filtered by suction on round filters. The egg clusters treated in this manner are subsequently laid out in Petri dishes and kept in darkness. After 6 to 8 days, the hatching rate compared with that of untreated control clusters is determined. The criterion for the evaluation is the minimum concentration of active ingredient required to effect a 100% destruction of the eggs.

Compounds according to Example 1 and Table 1 exhibit in this test a good ovicidal action against the pests examined. The compounds Nos. 2, 4, 5, 6 and 7 effect a 100% mortality rate at a concentration of active ingredient of 200 ppm, whilst the remaining compounds are fully effective at 800 ppm.

EXAMPLE 9

Action on *Laspeyresia pomonella*

Deposited Laspeyresia pomonella eggs, not more than 24 hours old, are immersed on filter paper for 1 minute in an acetonic/aqueous solution containing 400 ppm of the active ingredient to be tested. After the drying of the solution on the eggs, they are laid out in Petri dishes and kept at a temperature of 28° C. The percentage hatching rate from the treated eggs is evaluated after six days.

Compounds according to Example 1 and Table 1 result in no emergence of larvae occurring.

EXAMPLE 10

Chemosterilising action against *Anthonomus grandis*

Adult Anthonomus grandis, which have been hatched no longer than 24 hours, are transferred, in groups each of 25 beetles, to cages having lattice walls. The cages containing the beetles are then immersed for 5 to 10 seconds in an acetonic solution containing 1.0 percent by weight of the active ingredient to be tested. After the beetles are again dry, they are placed, for copulation and oviposition, into covered dishes containing feed. Deposited eggs are flushed out with running water two or three times weekly; they are counted, disinfected by being placed for two to three hours in an aqueous disinfectant (such as "Actamer B 100"), and then deposited into dishes containing a suitable larval diet. The eggs are examined after 7 days to determine whether larvae have developed from the deposited eggs.

In order to ascertain the duration of the chemosterilant effect of the active ingredients tested, the oviposition of the beetles is observed during a period of about four weeks. The evaluation is on the basis of the reduction in the number of eggs laid and hatched larvae in comparison with that of untreated control specimens.

Compounds according to Example 1 and Table 1 effect after 4 weeks a 90% reduction in the number of deposited eggs, and prevent to the extent of 100% the emergence of larvae, in the above test.

What is claimed is:

1. A compound of the formula

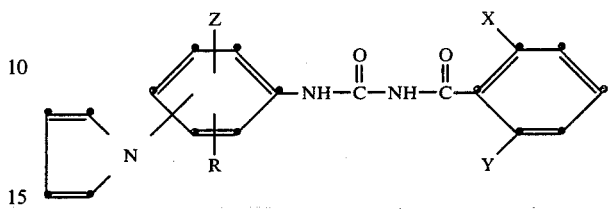

in which

X and Y independently of one another are each hydrogen or halogen,

R is hydrogen or halogen, and

Z is hydrogen, halogen or methyl.

2. A compound according to claim 1 of the formula

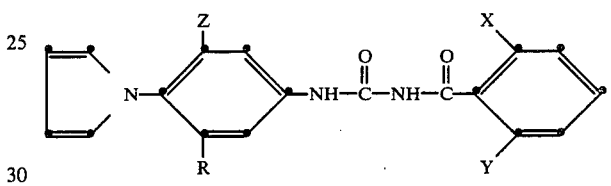

in which X is fluorine or chlorine, Y is hydrogen or fluorine, and R and Z are chlorine.

3. A pesticidal composition containing as active ingredient an effective anount of a compound according to claim 1, together with suitable carriers and/or further additives.

4. A process for controlling insects and members of the order Acarina in all stages of development, which process comprises applying a compound according to claim 1 to said insects or members of the order Acarina and/or to the locus thereof.

5. The compound of claim 2 wherein X and Y is fluorine.

6. The compound of claim 2 wherein X is chlorine and Y is fluorine.

7. The compound of claim 2 wherein X is chlorine and Y is hydrogen.

8. The compound of claim 2 wherein X is fluorine and Y is hydrogen.

* * * * *